United States Patent [19]

Benedict et al.

[11] Patent Number: 4,939,131

[45] Date of Patent: Jul. 3, 1990

[54] CERTAIN CYCLOALKANE-1,1-DIPHOSPHONIC ACIDS AND DERIVATIVES THEREOF HAVING THE ABILITY TO TREAT DISEASES ASSOCIATED WITH ABNORMAL CALCIUM AND PHOSPHATE METABOLISM

[75] Inventors: James J. Benedict; Karen Y. Johnson, both of Cincinnati, Ohio

[73] Assignee: The Procter & Gamble Company, Cincinnati, Ohio

[21] Appl. No.: 85,906

[22] Filed: Aug. 14, 1987

Related U.S. Application Data

[62] Division of Ser. No. 684,544, Dec. 21, 1984, Pat. No. 4,687,768.

[51] Int. Cl.$^5$ .......................... C07F 9/38; A61K 31/66
[52] U.S. Cl. ...................................... 514/102; 546/23; 558/161; 562/13; 562/21
[58] Field of Search ................... 260/502.4 P; 514/102

[56] References Cited

U.S. PATENT DOCUMENTS

| | | | |
|---|---|---|---|
| 3,683,080 | 8/1972 | Francis | 514/107 |
| 3,941,772 | 3/1976 | Ploger et al. | 546/6 |
| 3,960,888 | 6/1976 | Ploger et al. | 548/412 |
| 3,988,443 | 10/1976 | Ploger et al. | 514/79 |
| 4,034,086 | 7/1977 | Ploger et al. | 514/91 |
| 4,086,334 | 4/1978 | Schmidt-Dunker et al. | 514/11 |
| 4,104,366 | 8/1978 | Schmidt-Dunker et al. | 424/1.1 |
| 4,330,537 | 10/1980 | Francis | 514/105 |

OTHER PUBLICATIONS

Chem. Abstracts, vol. 92, (15), Abst. No. 123,437e, Apr. 14, 1980.
Mustafa et al., *Liebigs Ann. Chem.*, 698, 109 (1966).
Gross et al., *Liebigs Ann. Chem.*, 707, 35 (1967).

*Primary Examiner*—Alan L. Rotman
*Attorney, Agent, or Firm*—David L. Suter; Kim William Zerby; Jack D. Schaeffer

[57] ABSTRACT

Novel cyclic geminal-diphosphonic acid compounds, and pharmaceutical compositions containing these compounds, which are useful for treating diseases characterized by abnormal calcium and phosphate metabolism; and a method of treating diseases characterized by abnormal calcium and phosphate metabolism utilizing these novel cyclic diphosphonic acid compounds.

24 Claims, No Drawings

CERTAIN CYCLOALKANE-1,1-DIPHOSPHONIC ACIDS AND DERIVATIVES THEREOF HAVING THE ABILITY TO TREAT DISEASES ASSOCIATED WITH ABNORMAL CALCIUM AND PHOSPHATE METABOLISM

This is a division of application Ser. No. 684,544, filed on Dec. 21, 1984, now U.S. Pat. No. 4,687,768.

TECHNICAL FIELD

This invention relates to novel compounds which are useful in treating or preventing diseases characterized by abnormal calcium and phosphate metabolism, in particular those which are characterized by abnormal bone metabolism. This invention further relates to pharmaceutical compositions which contain the novel compounds of the present invention, and to a method of treating or preventing diseases characterized by abnormal calcium and phosphate metabolism utilizing a compound of the present invention.

BACKGROUND OF THE INVENTION

A number of pathological conditions which can afflict warm-blooded animals involve abnormal calcium and phosphate metabolism. Such conditions may be divided into two broad categories.

1. Conditions which are characterized by anomalous mobilization of calcium and phosphate leading to general or specific bone loss, or excessively high calcium and phosphate levels in the fluids of the body. Such conditions are sometimes referred to herein as pathological hard tissue demineralizations.

2. Conditions which cause or result from deposition of calcium and phosphate anomalously in the body. These conditions are sometimes referred to herein as pathological calcifications.

The first category includes osteoporosis, a condition in which bone hard tissue is lost disproportionately to the development of new hard tissue. Marrow and bone spaces become larger, fibrous binding decreases, and compact bone becomes fragile. Osteoporosis can be subclassified as menopausal, senile, drug induced (e.g., adrenocorticoid, as can occur in steroid therapy), disease-induced (e.g., arthritic and tumor), etc., however, the manifestations are essentially the same. Another condition in the first category is Paget's disease (osteitis deformans). In this disease, dissolution of normal bone occurs which is then haphazardly replaced by soft, poorly mineralized tissue such that the bone becomes deformed from pressures of weight bearing, particularly in the tibia and femur. Hyperparathyroidism, hypercalcemia of malignancy, and osteolytic bone metastases are conditions also included in the first category.

The second category, involving conditions manifested by anomalous calcium and phosphate deposition, includes myositis ossificans progressiva, calcinosis universalis, and such afflictions as arthritis, neuritis, bursitis, tendonitis and other inflammatory conditions which predispose involved tissue to deposition of calcium phosphates.

Polyphosphonic acids and their pharmaceutically-acceptable salts have been proposed for use in the treatment and prophylaxis of such conditions. In particular, diphosphonates like ethane-1-hydroxy-1,1-diphosphonic acid (EHDP), propane-3-amino-1-hydroxy-1,1-diphosphonic acid (APD), and dichloromethane diphosphonic acid ($Cl_2MDP$) have been the subject of considerable research efforts in this area. Paget's disease and heterotopic ossification are currently successfully treated with EHDP. The diphosphonates tend to inhibit the resorption of bone tissue, which is beneficial to patients suffering from excessive bone loss. However, EHDP, APD and many other prior art diphosphonates have the propensity of inhibiting bone mineralization when administered at high dosage levels.

It is therefore an object of this invention to provide novel diphosphonate compounds which inhibit the resorption of bone tissue and have a reduced propensity of inhibiting bone mineralization. It is a further object of this invention to provide compositions for the treatment and prophylaxis of abnormal calcium and phosphate metabolism. It is a still further object of this invention to provide an improved method for treating diseases characterized by abnormal calcium and phosphate metabolism.

BACKGROUND ART

The preparation of the tetraethyl ester of xanthane-9,9-diphosphonic acid is disclosed in Mustafa et al., Ann., 698, 109 (1966). The synthesis of the diphosphonomethylene ether of 1,2 dihydroxybenzene is disclosed in Gross et al., Liebigs Ann. Chem., 707, 35 (1967). Neither reference discloses a specific utility for the compounds described therein.

U.S. Pat. No. 3,683,080, issued Aug. 8, 1972 to Francis, discloses compositions comprising polyphosphonates, in particular diphosphonates, and their use in inhibiting anomalous deposition and mobilization of calcium phosphate in animal tissue.

U.S. Pat. No. 4,330,537, issued Oct. 28, 1980 to Francis, discloses compositions comprising certain phosphonate compounds in combination with vitamin D-like compounds for use in inhibiting mobilization of calcium phosphate in animal tissue. Among the phosphonate compounds disclosed therein are cycloalkyl-substituted hydroxymethane diphosphonates and vicinal diphosphonates of fluorinated cycloalkenes.

U.S. Pat. No. 3,988,433, issued Oct. 26, 1976 to Ploger et al., discloses azacycloalkane-2,2-diphosphonic acids. The compounds are said to be useful as sequestering agents, as stabilizers for percompounds, in delaying the setting of gypsum, in preventing the formation of tartar and plaque, and in the treatment of diseases related to the abnormal deposition or dissolution of difficultly soluble calcium salts in the animal body.

SUMMARY OF THE INVENTION

The present invention relates to specific geminal diphosphonic acid compounds which fall within the class of substituted and/or unsubstituted cyclopropane-1,1-diphosphonic acids, cyclobutane-1,1-diphosphonic acids, cyclopentane-1,1-diphosphonic acids, cyclopentene-1,1-diphosphonic acids, cyclohexane-1,1-diphosphonic acids, cyclohexene-1,1-diphosphonic acids, and cycloheptane-1,1-diphosphonic acids; wherein the substituted diphosphonic acids may be substituted with one or more substituents selected from the group consisting of substituted and unsubstituted alkyl (saturated or unsaturated) having from 1 to about 6 carbon atoms, substituted and unsubstituted aryl, substituted and unsubstituted benzyl, hydroxy, halogen, carboxyl, carbonyl, alkoxy, nitro, amido, amino, substituted amino, carboxylate, or combinations thereof; and pharmaceutically-acceptable salts and esters of said diphosphonic acids.

The invention further encompasses pharmaceutical compositions comprising a diphosphonic acid compound of this invention, and a pharmaceutical carrier. The invention further encompasses a method of treating diseases characterized by abnormal calcium and phosphate metabolism, comprising administering to a human or animal in need of such treatment a safe and effective amount of a compound of the invention.

DETAILED DESCRIPTION OF THE INVENTION

The compounds of the present invention fall within the class of geminal cycloalkyl diphosphonic acids and the pharmaceutically-acceptable salts and esters thereof. The cycloalkane moiety of the compounds can be cyclopropane, cyclobutane, cyclopentane, cyclopentene, cyclohexane, cyclohexene, or cycloheptane. The ring may have one or more of the following substituents: substituted and unsubstituted alkyl (saturated or unsaturated) having from 1 to about 6 carbon atoms, substituted and unsubstituted aryl (e.g. phenyl and naphthyl), substituted and unsubstituted benzyl, hydroxy, halogen, carboxy, carbonyl (e.g., —CHO and —COCH$_3$), alkoxy, (e.g., methoxy and ethoxy), nitro, amido (e.g., —NHCOCH$_3$), amino, substituted amino (e.g., dimethylamino, methylamino, and diethylamino), carboxylate (e.g., —OCOCH$_3$), or combinations thereof. Additional substituents could be substituted or unsubstituted sulfide, sulfoxide, or sulfone. Preferred substituents are methyl, alkylamino, amino, chloro, hydroxy, and methoxy. If the substituents attached to the diphosphonate-containing ring are themselves substituted, the substitution on these groups may be one or more of the substituents listed above. The two phosphonate moieties are attached to the same carbon atom (geminal diphosphonic acids), which is a member of the ring structure.

In the case of the cyclopentyl compounds the ring may be fused with a benzene ring (as in indan-2,2-diphosphonic acid) or a pyridine ring (as in dihydro-1-pyridine-6,6-diphosphonic acid), which itself may be substituted with one or more of the above-listed substituents. A benzene or pyridine ring imparts lipophilicity to the compounds, which is a desirable property in pharmaceutical compounds for systemic administration. The indan-2,2-diphosphonates are preferred compounds of the present invention.

The geminal diphosphonic acid containing ring can also be fused with a saturated or partially unsaturated ring (e.g., cyclopentane diphosphonic acid fused with cyclohexane (i.e. hexahydroindan-2,2-diphosphonic acid), and cyclopropyl diphosphonic acid fused with cyclohexane), which itseelf can be unsubstituted or substituted with one or more of the above listed substituents. The hexahydroindan-2,2-diphosphonic acids are preferred compounds of the present invention.

The present invention specifically relates to compounds of the structure:

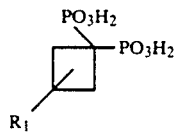

wherein R$_1$ is one or more substituents selected from the group consisting of substituted or unsubstituted alkyl (saturated or unsaturated) having from 1 to about 6 carbon atoms (with methyl being preferred), substituted and unsubstituted aryl, substituted and unsubstituted benzyl, hydroxy, halogen, substituted and unsubstituted amino, amido, carboxy, carbonyl, carboxylate, alkoxy, and combinations thereof; or

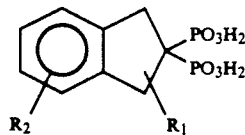

wherein R$_1$ is one or more substituents selected from the group consisting of hydrogen, substituted or unsubstituted alkyl (saturated or unsaturated) having from 1 to about 6 carbon atoms (preferred alkyl is methyl; preferred as substituents on the alkyl groups are substituted and unsubstituted amino, and amides thereof), substituted and unsubstituted aryl, substituted and unsubstituted benzyl, hydroxy, halogen, substituted and unsubstituted amino, amido, carboxy, carbonyl, carboxylate, alkoxy, and combinations thereof; R$_2$ is one or more substituents selected from the group consisting of hydrogen, substituted or unsubstituted alkyl (saturated or unsaturated) having from 1 to about 6 carbon atoms (preferred alkyl is methyl; preferred as substituents on the alkyl groups are substituted and unsubstituted amino, and amides thereof), substituted and unsubstituted aryl, substituted and unsubstituted benzyl, hydroxy, halogen, substituted and unsubstituted amino, amido, carboxy, carbonyl, carboxylate, alkoxy, nitro and combinations thereof; or

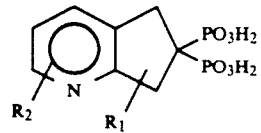

wherein R$_1$ is one or more substituents selected from the group consisting of hydrogen, substituted or unsubstituted alkyl (saturated or unsaturated) having from 1 to about 6 carbon atoms (preferred alkyl is methyl; preferred as substituents on the alkyl groups are substituted and unsubstituted amino, and amides thereof), substituted and unsubstituted aryl, substituted and unsubstituted benzyl, hydroxy, halogen, substituted and unsubstituted amino, amido, carboxy, carbonyl, carboxylate, alkoxy, and combinations thereof; R$_2$ is one or more substituents selected from the group consisting of hydrogen, substituted or unsubstituted alkyl (saturated or unsaturated) having from 1 to about 6 carbon atoms (preferred alkyl is methyl; preferred as substituents on the alkyl groups are substituted and unsubstituted amino, and amides thereof), substituted and unsubstituted aryl, substituted and unsubstituted benzyl, hydroxy, halogen, substituted and unsubstituted amino, amido, carboxy, carbonyl, carboxylate, alkoxy, nitro and combinations thereof; or

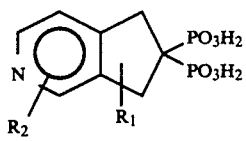

wherein R₁ is one or more substituents selected from the group consisting of hydrogen, substituted or unsubstituted alkyl (saturated or unsaturated) having from 1 to about 6 carbon atoms, substituted and unsubstituted aryl, substituted and unsubstituted benzyl, hydroxy, halogen, substituted and unsubstituted amino, amido, carboxy, carbonyl, carboxylate, alkoxy, and combinations thereof; R₂ is one or more substituents selected from the group consisting of hydrogen, substituted or unsubstituted alkyl (saturated or unsaturated) having from 1 to about 6 carbon atoms (preferred alkyl is methyl; preferred as substituents on the alkyl groups are substituted and unsubstituted amino, and amides thereof), substituted and unsubstituted aryl, substituted and unsubstituted benzyl, hydroxy, halogen, substituted and unsubstituted amino, amido, carboxy, carbonyl, carboxylate, alkoxy, nitro and combinations thereof; or

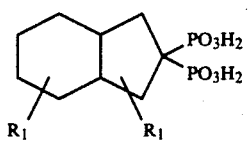

wherein R₁ is one or more substituents selected from the group consisting of hydrogen, substituted or unsubstituted alkyl (saturated or unsaturated) having from 1 to about 6 carbon atoms (preferred alkyl is methyl; preferred as substituents on the alkyl groups are substituted and unsubstituted amino, and amides thereof), substituted and unsubstituted aryl, substituted and unsubstituted benzyl, hydroxy, halogen, substituted and unsubstituted amino, amido, carboxy, carbonyl, carboxylate, alkoxy, and combinations thereof; or

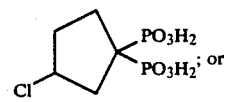

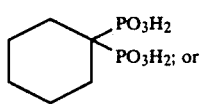

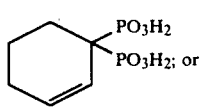

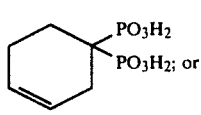

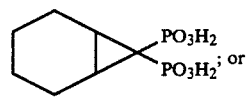

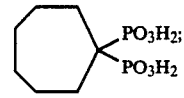

and the pharmaceutically-acceptable salts and esters of these compounds.

By "pharmaceutically-acceptable salts and esters" as used herein is meant hydrolyzable esters and salts of the diphosphonate compounds which have the same general pharmacological properties as the acid form from which they are derived, and which are acceptable from a toxicity viewpoint. Pharmaceutically-acceptable salts include alkali metal (sodium and potassium), alkaline earth metal (calcium and magnesium), non-toxic heavy metal (stannous and indium), and ammonium and low molecular weight substituted ammonium (mono-, di- and triethanolamine) salts. Preferred compounds are the sodium, potassium, and ammonium salts.

The compounds of the present invention are useful in the treatment of conditions in humans and animals characterized by abnormal calcium and phosphate metabolism. Other diphosphonates have been suggested for such use, in particular ethane-1-hydroxy-1,1-diphosphonate (EHDP), propane-3-amino-1-hydroxy-1,1-diphosphonate (APD), and dichloromethane diphosphonic acid (Cl₂MDP).

Although metabolic bone disorders have successfully been treated with the above art-disclosed diphosphonates, EHDP and APD have the tendency to inhibit bone mineralization as well as bone resorption. Administration of these compounds must therefore be carefully monitored in order to maximize bone resorption inhibition while avoiding inhibition of bone mineralization.

It has been discovered that in vitro cyclic diphosphonates generally have a much reduced potency for bone mineralization inhibition when compared to EHDP and APD. It has also been discovered that certain cyclic diphosphonates in vivo inhibit the resorption of bone tissue. Thus, at equally effective doses for inhibition of bone resorption, the compounds of the present invention are expected to inhibit bone mineralization to a lesser extent than many art-disclosed diphosphonates. The compounds of this invention therefore allow flexibility in the treatment of patients suffering from abnormal calcium and phosphate metabolism. The compounds of the present invention are also useful as bone scanning agents after labeling with 99m-Technetium.

The compounds of the present invention are also useful as sequestering agents for polyvalent metal ions, particularly di- and tri-valent metal ions, and therefore may be used for many technical applications, such as builders in detergents and cleansers, as well as in water treatment. They also may be used as stabilizers for percompounds. Other uses for the diphosphonic acids of the present invention are apparent to one skilled in the art.

Specific examples of compounds of the present invention include: 2-methylcyclobutane-1,1-diphosphonic acid; 3propylcyclobutane-1,1-diphosphonic acid; 2-hydroxycyclobutane-1,1-diphosphonic acid; 3- fluorocyclobutane-1,1-diphosphonic acid; 2-carboxycyclobutane-1,1-diphosphonic acid; indan-2,2-diphosphonic acid; 5,6-dimethylindan-2,2-diphosphonic acid; 4,5,6,7-tetramethylindan-2,2-diphosphonic acid; 4,5,6,7-tetrahydroxyindan-2,2-diphosphonic acid; 1-aminoindan-2,2-diphosphonic acid; 1-chloroindan-2,2-diphosphonic acid; 1,3-dichloroindan-2,2-diphosphonic acid; 4-(aminomethyl)-indan-2,2-diphosphonic acid; dihydro-1-pyrindine-6,6-diphosphonic acid; 2-chloro-dihydro-1-pyrindine-6,6-diphosphonic acid; 4-methoxy-dihydro-1-pyrindine-6,6-diphosphonic acid; 5-amino-dihydro-1-pyrindine-6,6-diphosphonic acid; dihydro-2-pyrindine-6,6-diphosphonic acid; 4-chloro-dihydro-2-pyrindine-6,6-diphosphonic acid; 7-methyl-dihydro-2-pyrindine-6,6-diphosphonic acid; 1-(aminomethyl)-dihydro-2-pyrindine-6,6-diphosphonic acid; hexahydroindan-2,2-diphosphonic acid; 1-hydroxyhexahydroindan-2,2-diphosphonic acid; 4-aminohexahydroindan-2,2-diphosphonic acid; 4-(aminomethyl)-hexahydroindan-2,2-diphosphonic acid; 1,5-dimethyl-hexahydroindan-2,2-diphosphonic acid; 3-chlorocyclopentane-1,1-diphosphonic acid; cyclohexane-1,1-diphosphonic acid; cyclohex-2-ene-1,1-diphosphonic acid; cyclohex-3-ene-1,1-diphosphonic acid; cycloheptane-1,1-diphosphonic acid; and pharmaceutically-acceptable salts and esters thereof.

Preferred compounds are indan-2,2-diphosphonic acid; hexahydroindan-2,2-diphosphonic acid; 2-methylcyclobutane-1,1-diphosphonic acid; 3-chlorocyclopentane-1,1-diphosphonic acid; cyclohexane-1,1-diphosphonic acid; and pharmaceutically-acceptable said and esters thereof.

CRYSTAL GROWTH INHIBITION TEST

The relative affinity of cyclic diphosphonates for calcified tissues is demonstrated by the crystal growth inhibition test. This test was developed for polyphosphonates to establish their potential to reduce calcium phosphate deposition and has been shown to be predictive of the affinity of these compounds for calcified tissues like bone. The test is described in detail by Nancollas, et al., *Oral Biol.*, 15, 731 (1970), the disclosures of which are incorporated herein by reference.

In this test, hydroxyapatite seed crystals are added to a calcium/phosphate solution supersaturated with respect to induced precipitation of calcium phosphates but meta-stable toward spontaneous precipitation. The seed crystals induce precipitation and crystal growth. Test chemicals are added to the meta-stable Ca/P solution before seeding. The effect of these chemicals on formation of hydroxyapatite induced by seed crystals has been shown to correlate with in vivo effects of these chemicals on calcium metabolism.

Formation of calcium phosphate crystals results in the release of hydrogen ions (i.e., pH change). The rate of crystal growth is monitored by observing the addition of base required to maintain a constant pH. Low levels ($1 \times 10^{-6}$M) of polyphosphonates are capable of inhibiting the formation of calcium phosphate for 20 minutes or longer. Crystal growth inhibition depends on the propensity of the polyphosphonates to adsorb on calcium phosphate crystal nuclei.

In the test, the time lapse, T, between addition of seed crystal and the start of crystal growth is measured. The effect of the presence of a diphosphonate compound is calculated as $$T_{lag} = T_{DP} - T_{contr}$$

wherein $T_{DP}$ is the time lapse for the experiment with $1 \times 10^{-6}$M of the diphosphonate compound present in the test solution, $T_{contr}$ is the time lapse in the experiment without diphosphonate, and $T_{lag}$ is the lag time resulting from the presence of the diphosphonate in the solution. For the present purpose, the lag times have been normalized ($T_n$; where $T_n$ (EHDP) = 1.0), by dividing the lag time for each compound by that measured for EHDP ($T_n = T_{lag}$ (test compound )/$T_{lag}$ (EHDP)). The $T_n$ values for various compounds are provided in Table 1.

It has been discovered that diphosphonates which possess low $T_{lag}$ values relative to EHDP in this test have a relatively low propensity for in vivo bone mineralization inhibition.

TABLE I

| Mineralization Inhibition (Crystal Growth Inhibition Test) | |
|---|---|
| Diphosphonate Compound | $T_n$ |
| EHDP[1] | 1.0 |
| APD[2] | 0.9 |
| Cl$_2$MDP[3] | 0.1 |
| Cyclobutane-1,1-DP | 0.2 |
| 2-Methylcyclobutane-1,1-DP* | 0.1 |
| Cyclopentane-1,1-DP | 0.3 |
| Cyclopent-3-ene-1,1-DP | 0.2 |
| 2-Methylcyclopentane-1,1-DP | 0.2 |
| 2,5-Dimethylcyclopentane-1,1-DP | 0.1 |
| 3-Hydroxycyclopentane-1,1-DP | 0.3 |
| 3-Chlorocyclopentane-1,1-DP* | 0.2 |
| Quinoxalino-2,3-cyclopentane-1,1-DP | 0.3 |
| Cyclohexane-1,1-DP* | 0.1 |
| 2-Methylcyclohexane-1,1-DP | 0.1 |
| 4-Methylcyclohexane-1,1-DP | 0.2 |
| Indan-2,2-DP* | 0.3 |
| 5,6-Dimethylindan-2,2-DP* | 0.3 |
| 4,5,6,7-Tetramethylindan-6,6-DP* | 0.3 |
| Dihydro-1-pyrindine-6,6-DP* | 0.3 |
| Hexahydroindan-2,2-DP* | 0.2 |

* = Compounds of the present invention
[1] Ethane-1-hydroxy-1,1-DP
[2] 3-Aminopropane-1-hydroxy-1,1-DP
[3] Dichloromethane-DP

SCHENK MODEL

The compounds were also evaluated for in vivo bone resorption inhibition and mineralization inhibition in an animal model system known in the field of bone metabolism as the Schenk Model. The general principles of this model system are disclosed in Shinoda et al., *Calcif. Tissue Int.*, 35, 87-99 (1983); and in Schenk et al., *Calcif. Tissue Res.* 11, 196-214 (1973), the disclosures of which are incorporated herein by reference.

MATERIALS AND METHODS

Animals

Preweaning 17-day-old (30 gms) male Sprague Dawley rats (Charles River Breeding Laboratories) were shipped with their mothers and placed in plastic cages with their mothers upon arrival. At 21 days of age, pups receiving Rat Chow and water ad libitum were randomly allocated into treatment groups comprising five animals per group, except for control animals receiving saline vehicle which had 10 rats per group. On day 0 and again on day 1 all animals were given a subcutaneous injection of Calcein (Sigma) as a 1% solution in 0.9% NaCl solution to label the skeleton.

Dose Solutions and Dosing Procedure

All solutions were prepared for subcutaneous injection in 0.9% normal saline and adjusted to pH 7.4 using NaOH and/or HCl. Dose solution calculation was made by considering the mass of powder (based on molecular weight, hydration) of the active material in mg/kg (body weight) that corresponds to mgP/kg. Concentrations were based on dosing 0.2 ml/100 g body weight. Initially, all compounds were administered at 0.1, 1.0 and 10.0 mg P/kg/day for 7 days. Compounds showing activity at 0.1 mg P/kg/day were then tested at logarithmic decrements down to 0.001 mg P/kg/day. Adjustments in dosage based on changes in body weight were made on a daily basis.

Necropsy, Tissue Processing and Histomorphometry

On day 8 after the start of dosing, all animals were sacrificed by $CO_2$ asphyxiation. Tibias were dissected free and placed in 70% ethyl alcohol. One tibia was dehydrated in graded ethanol solutions and embedded in methyl methacrylate using a rapid procedure described in Boyce et al., *Lab. Investig.*, 48, 683–689 (1983), the disclosures of which are incorporated herein by reference. The tibia was sectioned longitudinally through the metaphyseal area (Leitz ® saw microtome at 150μ). Specimens were stained on one surface with silver nitrate and mounted on microscope slides for evaluation with a Quantimet Image Analyzer (Cambridge Instruments, Inc.) using both incandescent and ultraviolet illumination. Metaphyseal trabecular bone content was measured in the region between the fluorescent label and the growth plate: expressed as percent of total area (bone+marrow). Epiphyseal growth plate width was obtained as the mean value of 10 equally-spaced measurements across the section.

Statistical evaluation of data was made using parametric and non-parametric analysis of variance and Wilcoxon's rank sum test to determine a statistically significant effect compared to control animals.

Diphosphonate compounds which have a bone mineralization inhibiting effect cause widening of the epiphyseal growth plate, since matrix production continues but mineralization is impeded. The widening of the epiphyseal growth plate as observed in the Schenk model is, therefore, a measure of the mineralization inhibiting effect of the diphosphonate compound tested (see Table II).

TABLE II

Mineralization Inhibition (Schenk Model)

| Diphosphonate Compound | Lowest tested dosage producing a statistically significant widening of epiphyseal growth plate (mg P/Kg) |
| --- | --- |
| EHDP[2] | 10 |
| APD[3] | 10 |
| Cl₂MDP[4] | — |
| Azacyclopentane-2,2-DP[5] | 10 |
| 5,6-Dimethylindan-2,2-DP* | —[1] |
| 4,5,6,7-Tetramethylindan-2,2-DP* | —[1] |
| Cyclopentane-1,1-DP | — |
| 3-Chlorocyclopentane-1,1-DP* | — |
| 2-Methylcyclopentane-1,1-DP | — |
| Indan-2,2-DP* | 10 |

\* = Compounds of the present invention
— = No plate widening observed at highest dose tested. (Highest dose tested is 10 mgP/Kg/day unless otherwise indicated.)
[1] Highest dose evaluated is 1 mgP/kg/day (compound lethally toxic at 10 mgP/kg/day)
[2] ethane-1-hydroxy-1,1-DP
[3] 3-amino propane-1-hydroxy-1,1-DP
[4] Dichloromethane DP
[5] A compound disclosed in U.S. Pat. No. 3,988,433, issued October 26, 1976, to Ploger et al.

Of the compounds tested, the prior art compounds EHDP, APD and azacyclopentane-2,2-DP show significant plate widening. Of the compounds of the present invention, only indan-2,2-DP caused significant plate widening. These results are in line with the crystal growth inhibition data (see Table I) which indicate that the compounds of the present invention possess moderate affinity for calcified tissues.

For the compounds for which plate widening was observed, the effect is quantified in Table III. The data are expressed as test/control ratio, i.e., the plate width observed for the test compound divided by the plate width observed in control experiments.

TABLE III

Epiphyseal Plate Width for Mineralization Observed by Schenk Model

| Compound | Epiphyseal Plate Width (test/control ratio) Dosage 10 mg P/kg |
| --- | --- |
| EHDP | 2.26 |
| APD | 2.12 |
| Azacyclopentane-2,2-DP | 2.38 |
| Indan-2,2-DP | 1.27 |

The data in Table III indicate that the magnitude of plate widening caused by indan-2,2-DP (the only compound of the present invention tested which caused such an effect) is significant but marginal compared to that caused by the prior art diphosphonate compounds which cause plate widening.

The Schenk model also provided data for in vivo bone resorption inhibition by the compounds. The lowest effective (antiresorptive) dose ("L.E.D.") for representative compounds, as determined by the Schenk model, are provided in Table IV along with the L.E.D. values as determined by the Thyroparathyroidectomized (TPTX) Rat Model.

Thyroparathyroidectomized (TPTX) Rat Model

The compounds were evaluated for in vivo bone resorption inhibition potency by an animal model system known as the thyroparathyroidectomized (TPTX) rat model. The general principles of this model system are disclosed in Russell et al., *Calcif. Tissue Research*, 6, 183–196 (1970), and in Muhlbauer and Fleisch, *Mineral Electrolyte Metab.*, 5, 296–303 (1981), the disclosures of which are incorporated herein by reference. The basic biochemical concept of the TPTX system is inhibition of the parathyroid hormone (PTH)—induced rise in serum and ionized calcium levels by the respective bone active polyphosphonates.

MATERIALS AND METHODS

Materials

Low calcium and low phosphorous diets used were prepared by Teklad® Test Diets (Harian Industries, Madison, Wis. 53711; Order #TD82195) in a pellet form of approximately 0.18% calcium and 0.22% phosphorous. The diets contained all the essential vitamins and minerals required for the rat, with the exception of calcium and phosphorous. The calcium and phosphorous levels of the pellets were verified analytically (Procter & Gamble Co., Miami Valley Laboratories, Cincinnati, Ohio).

PTH was acquired as a powdered bovine extract (Sigma Chemical Co., P.O. Box 14508, St. Louis, Mo., order #P-0892, Lot #72F-9650) at an activity of 138 USP units per mg. PTH was prepared in 0.9% saline such that the final concentration was 100 U.S.P./ml. All solutions were filtered through a #4 Whatman Filter Paper and refiltered through a 0.45 um Metricel® filter.

Dose Solutions and Dosing Procedure

All solutions of compounds to be tested for bone resorption inhibition potency were prepared for subcutaneous injection in 0.9% normal saline and adjusted to pH 7.4 using NaOH and/or HCl. Dose solution calculation was made by considering the mass of powder (based on molecular weight, hydration) of the active material in mg/kg (body weight) that corresponds to mg P/kg. Concentrations were based on dosing 0.2 ml/100 grams of body weight. Initially, all compounds were administered at 0.01, 0.1, and 1.0 mg P/kg/day for 4 days. Where necessary the test was repeated, whereby the animals were administered with 0.5 LED in order to refine the determination of LED. Adjustments in dosage based on changes in body weight were made on a daily basis.

Animals

In this study 50 male Wistar rats weighing approximately 150–160 grams were thyroparathyroidectomized surgically by the breeder (Charles River Breeding Laboratories). All rats were double housed on arrival in suspended cages with Purina Laboratory Rodent Chow® and tap water ad libitum. After acclimation to the laboratory environment for 3–5 days, the rats were placed on a low calcium, low phosphorous (0.18%/0.22%) diet (Tekland®) and given 2% (W/V) calcium gluconate supplemented deionized water via water bottles.

Method

On day four of low-calcium diet all rats were anesthetized with Ketaset® (Ketamine Hydrochloride, 100 mg/ml, Bristol Myers), 0.10 ml/100 grams of body weight, weighed and then bled from the retro-orbital venous plexus for serum total calcium analysis using Flame Atomic Absorption (FAA). All rats weighing less than 180 grams were eliminated from the study. Animals were then randomized statistically such that the mean total serum calcium for each group was the same. Only rats deemed hypocalcemic (total serum calcium $\leq 8.0$ mg/dl) were placed in study groups comprising six animals per group.

Treatments with the various experimental compounds commenced on day 6 and lasted through day 9 of the study (at 1:00 P.M. each day). Dose solutions were prepared to be given at a constant rate of 0.2 ml/100 grams of body weight subcutaneously in the ventral skin flap where the hind leg meets the torso. All rats were weighed and dosed daily. A 25 gauge ⅝" needle was used to administer drug, alternating dose sites daily. On day 8, animals were changed to deionized, distilled water via water bottles. On day 9 all rats were fasted in the afternoon at approximately 4:00 P.M. On day 10 of study no treatment was given. In the morning a 600 $\mu$l sample of whole blood was collected from each rat in Microtainer (B-D#5060) serum separater tubes for serum total calcium (FAA). Two 125 $\mu$l samples of heparinized whole blood were also collected to be used for ionized calcium analysis. Immediately following blood collection all rats were weighed and injected with bovine parathyroid hormone subcutaneously at a rate of 75 USP (filtered) per 100 grams of body weight. Blood sampling for total and ionized calcium was repeated three and one-half hours post-PTH injection.

All pre- and post-PTH total and ionized calciums were statistically analyzed for significance compared to PTH alone (control) using Student's t-test, analysis of variance, and their non-parametric equivalents. The post minus pre-charge and % change were also determined on calcium levels and pre-drug vs post-drug body weights.

The physiological effect of the PTH challenge is a rise in serum calcium level, with peak activity observed at three and one-half hours. Since the hormonal and dietary controls of calcium metabolism are minimized in the TPTX model, an observed increase in serum calcium level is presumably the result of resorption of bone material. Since polyphosphonates tend to inhibit resorption of bone materials, the animals pretreated with polyphosphonate showed a rise in serum calcium level after PTH challenge which was less than that found in control animals which had been treated with saline vehicle instead. The lowest dose at which the polyphosphonate is capable of inhibiting bone resorption, as evidenced by a decreased rise in serum calcium upon PTH challenge, is a measure of the bone resorption inhibition potency of the polyphosphonate. The LED values of the bone resorption inhibition potency of representative compounds as determined by the TPTX rat model and the Schenk model are presented in Table IV. The data in Table IV show that while the claimed diphosphonic acid compounds of the present invention inhibit resorption of bone material, there are closely related cyclic diphosphonic acid compounds which, in fact, do not exhibit this property.

TABLE IV

| | Lowest Effective (Antiresorptive) Dose | |
|---|---|---|
| Diphosphonate Compound | TPTX (mgP/kg) | Schenk (mgP/kg) |
| EHDP[2] | 1.0 | 1.0 |
| APD[3] | 0.1 | 0.1 |
| Cl$_2$MDP[4] | 1.0 | 1.0 |
| Azacyclopentane-2,2-DP[5] | N | N |
| Cyclobutane-1,1-DP | N | — |
| 2-Methylcyclobutane-1,1-DP* | 1.0 | — |
| Cyclopentane-1,1-DP | N | N |
| 2-Methylcyclopentane-1,1-DP | 10 | N |
| 2,5-Dimethylcyclopentane-1,1-DP | N | — |
| 3-Hydroxycyclopentane-1,1-DP | N | — |
| 3-Chlorocyclopentane-1,1-DP* | N | 1.0 |
| Quinoxalino-2,3-cyclopentane-1,1-DP | N | — |
| Cyclohexane-1,1-DP* | 1.0 | 10 |
| 2-Methylcyclohexane-1,1-DP | N | — |
| 4-Methylcyclohexane-1,1-DP | N | — |

TABLE IV-continued

Lowest Effective (Antiresorptive) Dose

| Diphosphonate Compound | TPTX (mgP/kg) | Schenk (mgP/kg) |
| --- | --- | --- |
| Indan-2,2-DP* | 0.5 | 1.0 |
| 5,6-Dimethylindan-2,2-DP* | 1.0 | 0.1[1] |
| 4,5,6,7-Tetramethylindan-2,2-DP* | 0.1 | 1.0[1] |
| Hexahydroindan-2,2-DP* | 1.0 | 1.0 |
| Cylopent-3-ene-1,1-DP | N | — |

\* = Compounds of the present invention
— = Not Tested
N = No activity
[1]Highest dose evaluated is 1 mg/P/kg/day (compound lethally toxic at 10 mgP/kg/day)
[2]ethane-1-hydroxy-1,1-DP
[3]3-amino propane-1-hydroxy-1,1-DP
[4]dichloromethane DP
[5]A compound disclosed in U.S. Pat. No. 3,988,433, issued October 26, 1976, to Ploger et al.

SYNTHESIS OF CYCLIC DIPHOSPHONATE COMPOUNDS

The synthesis reaction is carried out in the following way: In a first step, a methane diphosphonate ester, in solution, is converted to the corresponding carbanion using standard organic chemistry techniques. In a second step, to this reaction mixture is added a solution of a hydrocarbon compound suitably activated for a double nucleophilic substitution.

Typically, a solution of methane diphosphonate ester will be added to a cold suspension of potassium hydride in an inert organic solvent, and the solution left to stir at room temperature for a while. The suitably activated hydrocarbon will next be added as a solution to the reaction mixture, and the entire mixture then be heated to about 80° C. until completion. After the mixture has been cooled, filtered, and concentrated, the concentrate is chromatographed on silica gel to obtain the desired ester. The ester is hydrolyzed by refluxing in HCl and the resulting material concentrated under vacuum. The residue is dissolved in $H_2O$ and treated with activated charcoal. Following filtration, the solution is concentrated, and the product is finally dried under vacuum. Synthesis of salts and esters of these compounds is achieved using standard organic chemistry techniques well-known to those skilled in the art.

Following are examples of the synthesis of specific cyclic diphosphonates of this invention. The compounds were identified by $^1H$ NMR using $Me_4Si$ or sodium 2,2-dimethyl-2-silapentane-5-sulfonate as internal standards, and by $^{31}P$ NMR using $H_3PO_4$ as an external standard (positive values denote a chemical shift downfield from the reference); by chemical ionization mass spectrometry; by melting point determination; and by elemental analysis.

EXAMPLE I

Synthesis of Cyclohexane-1,1-diphosphonic acid

To a stirred, ice-cold suspension of potassium hydride (1.66 g of a 35% mineral oil dispersion, 14.5 mmol) in 20 mL of dry toluene was added dropwise a solution of tetraisopropyl methanediphosphonate (5.00 g, 14.5 mmol) in 50 mL toluene. Upon completion of addition, the ice-bath was removed and the clear yellow solution stirred at room temperature for 1 h. 1,5-Dibromopentane (1.67 g, 7.3 mmol) was dissolved in 10 mL toluene and added to the reaction mixture. The mixture was heated to 80° C. for 18 h. and then cooled in an ice-bath, filtered, and concentrated. The concentrate was chromatographed (1:1 hexane:THF eluent) on silica gel to afford the desired ester as a white crystalline material (61% yield based on the dibromide): mp 36°-38.5° C.; $^1H$ NMR ($CDCl_3$) chemical shift 4.95-4.59 (m, 4H, CH), 2.19-1.94 (m, 4H, $CH_2$), 1.85-1.51 (m, 6H, $CH_2$), 1.34 (d, 24H, J=6 Hz, $CH_3$); $^{31}P$ NMR ($CDCl_3$) 25.6 ppm; EI mass spectrum m/e 412 ($M^+$). Anal. calcd. for $C_{18}H_{38}O_6P_2$: C, 52.42; H, 9.29; P, 15.02. Found: C, 52.55; H, 9.43; P, 15.09.

A 10% solution of the DP ester in 12N HCl was refluxed for 2 h. The solution was then concentrated under vacuum using additional $H_2O$ to remove the final traces of HCl. The residue was then dissolved in $H_2O$ and treated with activated charcoal. The charcoal was removed by filtration and the filtrate concentrated using ether to remove the last traces of $H_2O$. The product was then dried under vacuum at 50° C. for 24 h. Yield 93%; mp 239° C.; $^1H$ NMR ($D_2O$) chemical shift 2.04-1.56 (overlapping m, $CH_2$); $^{31}P$ NMR ($D_2O$) 26.8 ppm. Anal. calcd. for $C_6H_{14}O_6P_2$: C, 29.52; H, 5.78; P, 25.38. Found: C, 29.54; H, 6.02; P, 25.19.

EXAMPLE II

Synthesis of 2-methylcyclobutane-1,1-diphosphonic acid

Using the procedure of Example I, tetraisopropyl methane diphosphonate was converted to tetraisopropyl 2-methyl cyclobutane-1,1 diphosphonate by reaction with 1,3 dibromobutane at 80° C. for 4 hours. $^{31}P$ NMR ($CDCl_3$) chemical shift 24.1 ppm.

The ester was then hydrolyzed to the corresponding acid using the method described in Example I in 86.2% yield.

$^{31}P$ NMR ($D_2O$) chemical shift 24.5 ppm; $^{13}C$ NMR ($D_2O$) 45.0, 43.1, 41.1 (t), 34.8, 26.4, 22.7 and 18.0 ppm.

EXAMPLE III

Synthesis of 3-chlorocyclopentane-1,1 diphosphonic acid (a) Preparation of tetraisopropyl 3-hydroxycyclopentane-1,1-diphosphonate tetrahydropyran ether Using the procedure described in Example I tetraisopropyl methane diphosphonate was converted to the desired ester in 67% yield by reaction with the tetrahydropyran ether of 1,4-dibromobutan-2-ol at 80° C. for 18 h: clear, viscous oil; $^1H$ NMR ($CDCl_3$) chemical shift 5.17-4.58 (m, 5H, $OCHMe_2$ and OCHO), 4.26-3.95 (m, 1H), 3.86-3.79 (m, 1H), 3.68-3.35 (m, 1H), 2.68-1.79 and 1.99 (m plus s, 6H total), 1.65-1.52 (m, 6H), 1.35 (d, 24H, J=6 Hz, $CH_3$); $^{31}P$ NMR ($CDCl_3$) 26.2, 25.8, 25.6, 25.2 ppm; ammonia CI mass spectrum m/e 499 ($MH^+$). Anal. calcd for $C_{22}H_{44}O_8P_2$: C, 53.00; H, 8.90; P, 12.43. Found: C, 52.70; H, 9.10; P, 12.67.

(b) Preparation of tetraisopropyl 3-hydroxycyclopentane-1,1-diphosphonate

The protected tetraester (9.40 g, 18.9 mmol) described above was dissolved in 180 mL MeOH. A catalytic amount (100 mg) of p-toluenesulfonic acid was added and the mixture stirred for 2 hours at room temperature. The solution was then concentrated. The residue was dissolved in ether (100 mL), washed with satd. $NaHCO_3$ solution, and then washed with brine. The ethereal solution was dried, concentrated, and then chromatographed (1:1 THF:hexane) on silica gel to afford 7.18 g (92%) of the desired product as a clear oil:

$^1$H NMR (CDCl$_3$) chemical shift 4.88–4.65 (m, 4H, OCHMe$_2$), 4.72 (s, 1H), 4.56–4.25 (m, 1H), 2.82–2.02 (m, 4H), 2.02–1.77 (m, 2H), 1.37 and 1.34 (overlapping d, 24H, J=6 and 6 Hz, CH$_3$); $^{31}$P NMR (CDCl$_3$) 30.1, 30.0, 25.4, 25.3 ppm; ammonia Cl mass spectrum m/e 415 (MH+).

(c) Preparation of 3-chlorocyclopentane-1,1-diphosphonate, from tetraisopropyl 3-hydroxycyclopentane-1,1-diphosphonate Tetraisopropyl 3-hydroxycyclopentane-1,1-diphosphonate (3.00 g, 7.24 mmol) was dissolved in 50 mL dry CCl$_4$. Triphenylphosphine (3.80 g, 14.5 mmol) was added and the mixture was refluxed for 72 h. The mixture was filtered, concentrated, and the residue chromatographed (3:2 hexane:THF) on silica gel to afford 2.15 g (69%) of the desired product as a clear, viscous oil: $^1$H NMR (CDCl$_3$) chemical shift 4.97–4.68 (m, 4H, OCHMe$_2$), 4.24 (m, 1H, J=7 Hz, CHOH), 2.65–1.87 (m, 6H, ring CH$_2$), 1.36 (d, 24H, J=6 Hz, CH$_3$); $^{31}$P NMR (CDCl$_3$) 25.3, 24.9, 24.4, 24.0; ammonia Cl mass spectrum m/e 433, 435 (MH+).

The ester was then hydrolyzed in 93% yield to the corresponding acid using the procedure described in Example I.

mp 194°–195° C.; $^1$H NMR (D$_2$O) 4.35 (p, 1H, J=6 Hz, ClCH), 2.47–1.90 (overlapping m, 6H, CH$_2$); $^{31}$P NMR (D$_2$O) 25.8 ppm. Anal. calcd. for C$_5$H$_{11}$ClO$_6$P$_2$: C, 22.70; H, 4.19; Cl, 13.40; P, 23.42. Found: C, 22.44; H, 4.28; Cl, 10.07; P, 23.44. The analytical data given are the average values from two different samples of material. The low percentage of Cl found indicates some hydrolysis of the Cl group during the reaction.

EXAMPLE IV

Synthesis of cycloheptane-1,1-diphosphonic acid

Using the same procedure as in Example I, tetraisopropyl methane diphosphonic acid was converted to tetraisopropyl cycloheptane-1,1-diphosphonate by reaction with 1,6-dibromohexane at 80° C. for 18 h. $^{31}$P NMR (toluene) indicated that the reaction solution contained a mixture of the desired tetraisopropyl cycloheptane-1,1-diphosphonate (25.3 ppm) and octaisopropyl octane-1,1,8,8-tetraphosphonate (22.1 ppm). The compounds were separated by chromatography (1:1 hexane:THF eluent) on silica gel, and the desired ester was hydrolyzed using 6N refluxing hydrochloric acid as in Example I.

EXAMPLE V

Indan-2,2-diphosphonic acid

Using the procedure described in Example I, tetraisopropylmethanediphosphonate MDP was converted to the desired ester in 70% yield by reaction with dibromo-o-xylene at 80° C. for 3 h: mp 55°–57° C.; $^1$H NMR (CDCl$_3$) 7.15 (s, 4H, aromatic), 5.00–4.55 (m, 4H, CH), 3.60 (t, 4H, J=17.6 Hz, CH$_2$), 1.26 (t, 24H, J=6 Hz, CH$_3$); $^{31}$P NMR (CDCl$_3$) 24.7 ppm; Cl mass spectrum m/e 447 (MH+). Anal. calcd for C$_{21}$H$_{36}$O$_6$P$_2$: C, 56.49; H, 8.13; P, 13.88. Found: C, 56.71; H, 8.24; P, 14.18.

The ester was then hydrolyzed in 93% yield to the corresponding acid using the method described in Example I. 93% yield; mp 249°–251.5° C.; $^1$H NMR (D$_2$O) 7.27 (br s, 4H, aromatic), 3.57 (g, 4H, J=18 Hz, CH$_2$); $^{31}$P NMR (D$_2$O) 25.8 ppm. Anal. calcd. for C$_9$H$_8$O$_6$P$_2$: C, 38.86; H, 4.35; P, 22.27. Found: C, 38.95; H, 4.53; P, 22.36.

EXAMPLE VI

Synthesis of hexahydroindan-2,2-diphosphonic acid

To a stirred suspension of potassium hydride (1.16 g, 29 mmol) in dry toluene at room temperature was added dropwise 10.0 g (29 mmol) of tetraisopropyl methane disphosphonate. After stirring for one hour at room temperature, 6.33 g of the solid ditosylate of cis-1,2-cyclohexanedimethanol (15 mmol, prepared from cis-1,2-cyclohexanedimethanol and tosylchloride using a standard procedure described in Fieser and Fieser, p. 1179, the disclosures of which are incorporated herein by reference) was added. The reaction mixture was refluxed for 4 h, and cooled to room temperature overnight. The precipitate was filtered off and discarded. The toluene was evaporated off and the resulting oil (3.0 g) was chromatographed (35:65 acetone:hexane eluent) on silica gel. The 2.7 g of isolated tetraisopropyl ester of hexahydroindan-2,2-diphosphonic acid was added to 6N hydrochloric acid and refluxed overnight. The hydrochloric acid was removed by evaporation and the remaining solid was dissolved in 25 ml distilled water. The pH was then adjusted to 4.8 with 50% NaOH solution. The slow addition of ethanol and cooling resulted in the formation of a white precipitate. Filtration and drying yielded 1.2 g of the sodium salt of hexahydroindan-2,2-diphosphonic acid. $^{13}$C NMR (D$_2$O) 54.9 ppm (t, J=123 Hz), 41.2 ppm 40.9 ppm, 39.4 ppm, 30.2 ppm, and 26.1 ppm; $^{31}$P NMR (D$_2$O) "AB" quartet at 28.2 ppm, 22.9 ppm, 27.1 ppm and 26.8 ppm.

EXAMPLE VII

Synthesis of Dihydro-1-pyrindine-6,6-diphosphonic acid

To an ice bath chilled solution of 35% potassium hydride in mineral oil (5.2 g 0.045 moles) stirring under argon in 70 ml of DMSO (dry) was added a solution of tetraisopropylmethanediphosphonate (7.82 g, 0.023 moles) in 30 ml of DMSO. On completion of a dropwise addition the resulting solution was stirred at room temperature for one hour. A solution of 2,3-bis(chloromethyl)pyridine (4.0 g, 0.023 mole) (crude product as isolated by K. Tsuda et. al. Chem Pharm Bull 1, (1953) 142) in 15 ml of DMSO was slowly added and the reaction mixture was then heated at 90° C. for 1 hour. After cooling the DMSO was removed under vacuum. 2.1 g (21%)of the desired product was purified via flash chromatography using a 5–15% ethanol in methylene chloride gradient on silica gel. The resulting tan oil gave the following spectral characteristics:

$^1$H NMR (CDCl$_3$) 8.34 (d, 1H), 7.45 (d, 1H), 7.02 (dd, 1H), 4.77 (m, 4H), 3.58 (dt, 4H), 1.35 (d, 24H); $^{31}$P NMR (CDCl$_3$) 23.97 ppm (s).

The ester (1.92 g, 0.0043 mole) was added to 38 ml of 6N HCl, and then refluxed with stirring under an argon atmosphere for 18 hours. The resulting precipitate was filtered, rinsed with water (2×5 ml), and dried to yield 0.8 g (66.5%) of an off-white crystalline solid: mp>300° C. (dec); $^1$H NMR (D$_2$O/NaOD) 8.19 (d, 1H, J=3.4 Hz), 7.62 (d, 1H, J=7.5 Hz), 7.13 (dd, 1H, J=3.4 and 7.5 Hz), 3.46 (t, 4H, J=15.8 Hz); $^{31}$P NMR (D$_2$O/NaOD) 24.84 ppm (s).

EXAMPLE VIII

Synthesis of Dihydro-2-pyrindine-6,6-diphosphonic acid

Using the same procedure as in Example VII, tetraisopropyl methane diphosphonate is converted to tetraisopropyl dihydro-2-pyrindine-6,6-diphosphonate by reaction with 3,4-bis(chloromethyl)pyridine. The resulting ester is hydrolyzed as in Example VII to yield the dihydro-2-pyrindine-6,6-diphosphonic acid.

EXAMPLE IX

Synthesis of 3-cyclohexene-1,1-diphosphonic acid

Using the same procedure as in Example I, tetraisopropyl methane diphosphonate is converted to tetraisoproyl 3-cyclohexene-1,1-diphosphonate by reaction with 1,5-dichloro-cis-2-pentene. The resulting ester is hydrolyzed as in Example I to yield the 3-cyclohexene-1,1-diphosphonic acid.

EXAMPLE X

Synthesis of 2-cyclohexene-1,1-diphosphonic acid

Using the same procedure as in Example III, tetraethyl methane diphosphonate is converted to tetraethyl 3-hydroxycyclohexane-1,1-diphosphonate by reaction with the tetrahydropyran ether of 1,5-dibromopentan-2-ol, followed by hydrolysis of the ether with p-toluenesulfonic acid in MeOH. The resulting ester is dehydrated to the tetraethyl 2-cyclohexene-1,1-diphosphonate using the procedure discussed in Vogel: A Textbook of Practical Organic Chemistry 3rd Ed., p. 243, the disclosures of which are incorporated herein by reference. The tetraethyl ester is hydrolyzed to the desired 2-cyclohexene-1,1-diphosphonic acid by the dropwise addition of trimethyl silyl bromide to a solution of the tetraethyl ester in $CCl_4$ at room temperature.

EXAMPLE XI

Synthesis of

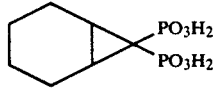

The desired phosphonic acid is synthesized by first reacting cyclohexene with a dibromocarbene precursor under phase-transfer conditions (see: Tetrahedron Letters 21, p. 1783 (1976), the disclosures of which are incorporated herein by reference) to generate

Reaction of the dibromide under traditional Arbuzov conditions (see: Topics in Phosphorous Chemistry 1, p. 57, Interscience 1964, the disclosures of which are incorporated herein by reference) generates the diphosphonate ester of the desired product. Hydrolysis with 6N HCl, or trimethyl silyl bromide for the tetraethyl ester, yields the desired diphosphonic acid.

Another aspect of this invention is a method for treating or preventing diseases characterized by abnormal calcium and phosphate metabolism, in particular those which are characterized by abnormal bone metabolism, in persons at risk to such disease, comprising the step of administering to persons in need of such treatment a safe and effective amount of a cyclic diphosphonate of the present invention. The preferred mode of administration is orally, but other modes of administration include, without limitation, transdermal, mucosal, sublingual, intramuscular, intravenous, intraperitoneal, and subcutaneous administration, as well as topical application.

By "abnormal calcium and phosphate metabolism" as used herein is meant (1) conditions which are characterized by anomalous mobilization of calcium and phosphate leading to general or specific bone loss, or excessively high calcium and phosphate levels in the fluids of the body; and (2) conditions which cause or result from deposition of calcium and phosphate anomalously in the body. The first category includes, but is not limited to, osteoporosis, Paget's disease, hyperparathyroidism, hypercalcemia of malignancy, and osteolytic bone metastases. The second category includes, but is not limited to, myositis ossificans progressiva, calcinosis universalis, and such afflictions as arthritis, neuritis, bursitis, tendonitis and other inflammatory conditions which predispose involved tissue to deposition of calcium phosphates.

By "person at risk", or "person in need of such treatment", as used herein is meant any human or lower animal which suffers a significant risk of abnormal calcium and phosphate metabolism if left untreated, and any human or lower animal diagnosed as being afflicted with abnormal calcium and phosphate metabolism. For example, postmenopausal women; persons undergoing certain steroid therapy; persons on certain anti-convulsant drugs; persons diagnosed as having Paget's disease, hyperparathyroidism, hypercalcemia of malignancy, or osteolytic bone metastases; persons diagnosed as suffering from one or more of the various forms of osteoporosis; persons belonging to a population group known to have a significantly higher than average chance of developing osteoporosis, e.g., postmenopausal women, men over age 65, and persons being treated with drugs known to cause osteoporosis as a side effect; persons diagnosed as suffering from myositis ossificans progressiva or calcinosis universalis; and persons afflicted with arthritis, neuritis, bursitis, tendonitis and other inflammatory conditions which predispose involved tissue to deposition of calcium phosphate.

By "human or lower animal afflicted with or at risk to osteoporosis" as used herein is meant a subject diagnosed as suffering from one or more of the various forms of osteoporsis, or a subject belonging to a group known to have a significantly higher than average chance of developing osteoporosis, e.g., postmenopausal women, men over the age of 65, and persons being treated with drugs known to cause osteoporosis as a side effect (such as adrenocorticoid).

By "safe and effective amount" as used herein is meant, within the scope of sound medical judgment, an amount of a compound or composition high enough to significantly positively modify the condition to be treated, but low enough to avoid serious side effects (at a reasonable benefit/risk ratio). The safe and effective amount of cyclic diphosphonates of the present invention will vary with the particular condition being treated, the age and physical condition of the patient being treated, the severity of the condition, the duration of treament, the nature of concurrent therapy, and the specific diphosphonate employed. However, single dosages can range from about 0.1 mg P to about 3500 mg P, or from about 0.01 to about 500 mg P/kg of body weight. Preferred single dosages are from about 5 mg P to about 600 mg P, or from about 0.5 to about 50 mg P/kg of body weight. Up to about four single dosages per day may be administered. Daily dosages greater than about 2000 mg P/kg are not required to produce the desired effect and may produce undesirable side effects. The higher dosages within this range are, of course, required in the case of oral administration because of limited absorption.

EXAMPLE XII

Patients weighing approximately 70 kg who are clinically diagnosed as suffering from hypercalcemia of malignancy are administered 350 mg P of hexahydroindan diphosphonic acid, or its pharmaceutically-acceptable salt or ester, orally 2 times daily for 3 months. This treatment results in an appreciable alleviation of the hypercalcemia of malignancy.

Similar results are achieved by using other diphosphonic acids of the present invention, or their pharmaceutically-acceptable salts or esters, e.g., indan-2,2-diphosphonic acid; 2-methylcyclobutane-1,1-diphosphonic acid; 3-chlorocyclopentane-1,1-diphosphonic acid; or cyclohexane-1,1-diphosphonic acid.

An additional aspect of this invention is a pharmaceutical composition comprising a safe and effective amount of diphosphonate of the present invention and a pharmaceutical carrier.

By "pharmaceutical carrier" as used herein is meant one or more compatible solid or liquid filler diluents or encapsulating substances. By "compatible" as used herein is meant that the components of the composition are capable of being commingled without interacting in a manner which would substantially decrease the efficacy of the total composition under ordinary use situations.

Some examples of the substances which can serve as pharmaceutical carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin, talc; stearic acid; magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; pyrogen-free water; isotonic saline; and phosphate buffer solutions, as well as other non-toxic compatible substances used in pharmaceutical formulations. Wetting agents and lubricants such as sodium lauryl sulfate, as well as coloring agents, flavoring agents and preservatives, can also be present. Other compatible pharmaceutical additives and actives may be included in the pharmaceutical compositions of the present invention.

The choice of a pharmaceutical carrier to be used in conjunction with the diphosphonate of the present invention is basically determined by the way the diphosphonate is to be administered. If the compound is to be injected, the preferred pharmaceutical carrier is sterile physiological saline, the pH of which has been adjusted to about 7.4. However, the preferred mode of administering the diphosphonates of the present invention is orally, and the preferred unit dosage form is therefore tablets, capsules and the like comprising from about 15 mg P to about 600 mg P of a diphosphonic acid compound of the present invention. Pharmaceutical carriers suitable for the preparation of unit dosage forms for oral administration are well kown in the art. Their selection will depend on secondary considerations like taste, cost, shelf stability, which are not critical for the purposes of the present invention, and can be made without difficulty by a person skilled in the art. The pharmaceutical carrier employed in conjunction with the diphosphonates of the present invention is used at a concentration sufficient to provide a practical size to dosage relationship. Preferably, the pharmaceutical carrier comprises from about 0.1% to about 99.9% by weight of the total composition.

EXAMPLE XIII

Capsules are prepared by conventional methods, comprised as follows:

| Ingredient | Mg per Capsule |
|---|---|
| Indan-2,2-DP | 350.00 (as mgP) |
| Starch | 55.60 |
| Sodium lauryl sulfate | 2.90 |

The above capsules administered orally twice daily for 6 months substantially reduce bone resorption in a patient weighing approximately 70 kilograms afflicted with osteoporosis. Similar results are obtained when indan-2,2-DP in the above-described capsules is replaced with hexahydroindan-2,2-DP; 2-methylcyclobutane-1,1-DP; 3-chlorocyclopentane-1,1-diphosphonic acid; and cyclohexane-1,1-DP, or a pharmaceutically acceptable salt or ester of these diphosphonate compounds.

What is claimed is:

1. A cyclic diphosphonic acid, or a pharmaceutically-acceptable salt thereof, having the structure:

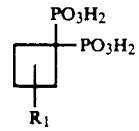

wherein $R_1$ is selected from the group consisting of alkyl having from 1 to 6 carbon atoms, substituted alkyl having from 1 to 6 carbon atoms, phenyl, substituted phenyl, naphthyl, substituted naphthyl, benzyl, substituted benzyl, hydroxy, halogen, amino, substituted amino, acyl amino having from 1 to 6 carbon atoms, carboxy, carbonyl, and alkoxy; and said substituted $R_1$ groups are substituted with a member selected from the group consisting of methyl, amino, $C_1$-$C_6$ alkylamino, chloro, hydroxy and methoxy.

2. 3-Chlorocyclopentane-1,1-diphosphonic acid, or a pharmaceutically-acceptable salt thereof.

3. Cyclohexane-1,1-diphosphonic acid, or a pharmaceutically-acceptable salt thereof.

4. Cyclohex-2-ene-1,1-diphosphonic acid, or a pharmaceutically-acceptable salt thereof.

5. Cyclohex-3-ene-1,1-diphosphonic acid, or a pharmaceutically-acceptable salt thereof.

6. Cycloheptane-1,1-diphosphonic acid, or a pharmaceutically-acceptable salt thereof.

7. 1-Methylcyclobutane-1,1-diphosphonic acid, or a pharmaceutically-acceptable salt thereof.

8. A pharmaceutical composition comprising:

(a) from 15 mg P to 600 mg P of a diphosphonic acid compound of claim 1; and
(b) a pharmaceutical carrier.

9. A pharmaceutical composition comprising:
(a) from 15 mg P to 600 mg P of a diphosphonic acid compound of claim 2; and
(b) a pharmaceutical carrier.

10. A pharmaceutical composition comprising:
(a) from 15 mg P to 600 mg P of a diphosphonic acid compound of claim 3; and
(b) a pharmaceutical carrier.

11. A pharmaceutical composition comprising:
(a) from 15 mg P to 600 mg P of a diphosphonic acid compound of claim 4; and
(b) a pharmaceutical carrier.

12. A pharmaceutical composition comprising:
(a) from 15 mg P to 600 mg P of a disphosphonic acid compound of claim 5; and
(b) a pharmaceutical carrier.

13. A pharmaceutical composition comprising:
(a) from 15 mg P to 600 mg P of a diphosphonic acid compound of claim 6; and
(b) a pharmaceutical carrier.

14. A pharmaceutical composition comprising:
(a) from 15 mg P to 600 mg P of a diphosphonic acid compound of claim 7; and
(b) a pharmaceutical carrier.

15. A method of treating diseases associated with abnormal calcium and phosphate metabolism, comprising administering to a person in need of such treatment a safe and effective amount of a compound of claim 1.

16. A method of treating diseases associated with abnormal calcium and phosphate metabolism, comprising administering to a person in need of such treatment a safe and effective amount of a compound of claim 2.

17. A method of treating diseases associated with abnormal calcium and phosphate metabolism, comprising administering to a person in need of such treatment a safe and effective amount of a compound of claim 3.

18. A method of treating diseases associated with abnormal calcium and phosphate metabolism, comprising administering to a person in need of such treatment a safe and effective amount of a compound of claim 4.

19. A method of treating diseases associated with abnormal calcium and phosphate metabolism, comprising administering to a person in need of such treatment a safe and effective amount of a compound of claim 5.

20. A method of treating diseases associated with abnormal calcium and phosphate metabolism, comprising administering to a person in need of such treatment a safe and effective amount of a compound of claim 6.

21. A method of treating diseases associated with abnormal calcium and phosphate metabolism, comprising administering to a person in need of such treatment a safe and effective amount of a compound of claim 7.

22. A method for treating osteoporosis in humans or lower animals comprising administering to a human or lower animal, afflicted with or at risk to osteoporosis, a safe and effective amount of a compound of claim 2.

23. A method for treating osteoporosis in humans or lower animals comprising administering to a human or lower animal, afflicted with or at risk to osteoporosis, a safe and effective amount of a compound of claim 3.

24. A method for treating osteoporosis in humans or lower animals comprising administering to a human or lower animal, afflicted with or at risk to osteoporosis, a safe and effective amount of a compound of claim 7.

* * * * *